(12) United States Patent
Huebner et al.

(10) Patent No.: US 9,290,531 B2
(45) Date of Patent: Mar. 22, 2016

(54) SYNTHETIC LTA MIMETICS AND USE THEREOF AS VACCINE COMPONENT FOR THERAPY AND/OR PROPHYLAXIS AGAINST GRAM-POSITIVE INFECTIONS

(75) Inventors: Johannes Huebner, Freiburg (DE); Andrea Huebner-Kropec, Freiburg (DE); Jeroen Dirk Cornelis Codée, Leiden (NL); Gijsbert Arie Van Der Marel, Leiden (NL); Wouter Frederick Johan Hogendorf, Leiden (NL)

(73) Assignee: UNIVERSITÄTSKLINIKUM FREIBURG, Freiburg (DE)

( * ) Notice: Subject to any disclaimer, the term of this patent is extended or adjusted under 35 U.S.C. 154(b) by 0 days.

(21) Appl. No.: 14/002,459

(22) PCT Filed: Feb. 17, 2012

(86) PCT No.: PCT/EP2012/052801
§ 371 (c)(1),
(2), (4) Date: Nov. 4, 2013

(87) PCT Pub. No.: WO2012/119846
PCT Pub. Date: Sep. 13, 2012

(65) Prior Publication Data
US 2014/0050741 A1    Feb. 20, 2014

Related U.S. Application Data

(60) Provisional application No. 61/451,304, filed on Mar. 10, 2011.

(30) Foreign Application Priority Data

Mar. 11, 2011    (EP) .................................... 11157947

(51) Int. Cl.
| A61K 39/02 | (2006.01) |
| C07H 15/04 | (2006.01) |
| A61K 39/385 | (2006.01) |
| C07F 9/11 | (2006.01) |
| C07K 16/12 | (2006.01) |

(52) U.S. Cl.
CPC .............. *C07H 15/04* (2013.01); *A61K 39/385* (2013.01); *C07F 9/11* (2013.01); *C07K 16/1267* (2013.01)

(58) Field of Classification Search
None
See application file for complete search history.

(56) References Cited

U.S. PATENT DOCUMENTS

| 6,214,978 B1 * | 4/2001 | Truog et al. ..................... 536/4.1 |
| 2006/0189550 A1 * | 8/2006 | Jiang et al. ....................... 514/26 |

OTHER PUBLICATIONS

Fukase et al. Synthetic Study of Lipoteichoic Acid of Gram Positive Bacteria. Bulletin of the Chemical Society of Japan. Feb. 1994, vol. 67, No. 2, pp. 473-482.*

Hogendorf, Wouter F. J, et al., "Synthesis of an α- kojibiosyl substituteg glycerol teichoic acid hexamer," *Bioorganic & Medicinal Chemistry*, Jun. 1, 2010, vol. 18, Issue 11, p. 3668-3678.

(Continued)

*Primary Examiner* — Jeffrey E Russel
(74) *Attorney, Agent, or Firm* — Saliwanchik, Lloyd & Eisenschenk

(57) ABSTRACT

The present invention relates to synthetic lipoteicoic acid (LTA) mimetics which are useful as vaccine components for therapy and/or prophylaxis of bacterial infection.

18 Claims, 3 Drawing Sheets

(56) References Cited

OTHER PUBLICATIONS

Huebner, Johannes et al., "Isolation and Chemical Characterization of a Capsular Polysaccharide Antigen Shared by Clinical Isolates of *Enterococcus faecalis* and Vancomycin-Resistant *Enterococcus faecalis*," *Infections and Immunity*, Mar. 1999, vol. 67, Issue 3, p. 1213-1219.

Theilacker, Christian et al., "Opsonic Antibodies *Enterococcus faecalis* Strain 12030 Are Directed against Lipoteichoic Acid," *Infections and Immunity*, Oct. 2006, vol. 74, Issue 10, p. 5703-5712.

Wang, Ying et al., "Structure of an antigenic teichoic acid shared by clinical isolates of *Enterococcus faecalis* and vancomycin-resistant *Enterococcus faecium*," *Carbohydrate Research*, Mar. 15, 1999, vol. 316, p. 155-160.

* cited by examiner

WH6

WH7

SYNTHETIC LTA MIMETICS AND USE THEREOF AS VACCINE COMPONENT FOR THERAPY AND/OR PROPHYLAXIS AGAINST GRAM-POSITIVE INFECTIONS

CROSS REFERENCE TO A RELATED APPLICATION

This application is a National Stage Application of International Application Number PCT/EP2012/052801, filed Feb. 17, 2012; which claims priority to U.S. Provisional Application No. 61/451,304, filed Mar. 10, 2011 and European Application No. 11157947.0, filed Mar. 11, 2011; all of which are incorporated herein by reference in their entirety.

The present invention relates to synthetic lipoteichoic acid (LTA) mimetics which are useful as vaccine components for therapy and/or prophylaxis of bacterial infection.

BACKGROUND OF THE INVENTION

*Enterococci* are among the most important pathogens associated with infections in hospitalized patients. Especially the presence of multiple antibiotic resistance determinants in most clinically relevant isolates urges the development of alternative treatment and prevention strategies to combat these sometimes untreatable infections. *Enterococci* have developed specific mechanisms to acquire and transmit DNA horizontally, and these traits are responsible for numerous outbreaks in the hospital setting.

At least 15 *enterococcal* species exist, but only two of them are commonly associated with clinical infection, namely, *Enterococcus faecalis*, which is responsible for 80% infections caused by *enterococci*, and *Enterococcus faecium*. The Gram-positive bacterium *Enterococcus faecalis* is a natural inhabitant of the mammalian gastrointestinal tract, and is commonly found in soil, sewage, water, and food, frequently through faecal contamination (Klare, I., Werner, G. and Witte, W. Contrib. Microbiol. 2001, 8, 108-22).

Sensitive strains of these bacteria can be treated with ampicillin and vancomycin. Nevertheless, some *enterococci* are resistant to β-lactam-based antibiotics (intrinsically against all cephalosporins and in some cases acquired against penicillins through a beta-lactamase) as well as aminoglycosides (intrinsic low-level resistance, acquired high-level resistance). In the last two decades, particularly virulent strains of *Enterococcus* that are resistant to vancomycin (Vancomycin-resistant *Enterococcus*, or VRE) have emerged in nosocomial infections of hospitalized patients especially in the US, but to a lesser extent also in countries all over the world. The increasing occurrence of *enterococcal* strains resistant to multiple antibiotics underscores the necessity to improve the understanding of the pathogenesis of infection (Murray, B. E. N. Engl. J. Med. 2000, 342, 710-721; Theilacker, C., Krueger, W. A., Kropec, A. and Huebner, J. Vaccine 2004, 22 Suppl 1, S31-8).

Teichoic acids can be found in the cell wall of gram-positive bacteria, such as *Staphylococci, Streptococci, Bacillus, Clostridium, Corynebacterium* and *Listeria*, and appear to protrude from the surface of the peptidoglycan layer. Teichoic acids are not found in gram-negative bacteria. They can be covalently linked to N-acetylmuramic acid of the peptidoglycan layer (wall teichoic acid, WTA), or attached via a lipid anchor in the cytoplasmic membrane (lipoteichoic acid, LTA).

The main function of teichoic acids is to provide rigidity to the cell-wall by attracting cations such as magnesium and sodium. Teichoic acids are usually, but not always, substituted with D-alanine ester residues, giving the molecule zwitterionic properties. These zwitterionic teichoic acids are suspected ligands for toll-like receptors 2 and 4. Teichoic acids also assist in regulation of cell growth by limiting the ability of autolysins to break the β(1-4) bond between the N-acetyl glucosamine and the N-acetylmuramic acid. Teichoic acids serve as an attachment site for some parasites. Destruction of the bacteria and release of the teichoic acid into the bloodstream may cause fever, blood vessel dilation and possibly shock and subsequent death. Teichoic acid can also be used by bacteria to attach to mucosal membranes.

*Enterococcal* LTA is a complex molecule consisting of a glycolipid anchor and a polyglycerol phosphate chain substituted non-stochiometrically with alanine, kojibiose, and alaninated kojibiose (Theilacker, Kaczynski et al. 2006). LTA is an integral component of the gram-positive cell wall, and antibodies against this antigen have been shown to be protective against *enterococcal* infections (Huebner, Wang et al. 1999; Huebner, Quaas et al. 2000; Theilacker, Kaczynski et al. 2006). However, the antigenic component constituting the protective epitope has been not defined so far. Structurally similar molecules exist in other clinically relevant gram-positive bacteria (such as *streptococci, staphylococci, listeria,* etc.) and rabbit immune sera raised against an *Enterococus faecalis* LTA has been shown to be protective also against *Streptococcus agalactiae* and *Staphylococcus aureus* (Huebner at el., unpublished observation).

Teichoic acids and lipoteichoic acids have been considered strong exogenous pyrogens, i.e. they belong to the substances that may lead to a feverish reaction in a human after a bacterial infection by gram-positive bacteria. They are most likely recognized by the toll-like receptor TLR-2 that is expressed on monocytes and dendritic cells, B- and T-lymphocytes and macro-phages. Furthermore, they lead to the excretion of cytokines, and therefore are one factor for the inflammatory reaction following such an infection.

Due to their antigenic properties, they have also been proposed as interesting candidates for the development of synthetic vaccines.

U.S. Pat. No. 7,011,826 describes a vaccine for the prevention of lactic acidosis in a vertebrate, said vaccine comprising at least one isolated microorganism, or fragment or fragments thereof, wherein said microorganism is capable of producing lactic acid within the gut of said vertebrate, and wherein said microorganism is selected from the group consisting of: *Clostridium*-like species, *Prevotella*-like species, *Bacteroides*-like species, *Enterococcus*-like species, and *Selenomonas* species.

Using structural information derived from above-mentioned studies, Hogendorf and colleagues recently synthesized mimetics of the *Enterococcus* glycerophosphate backbone (Hogendorf, Bos et al. 2010).

Morath et al (in Morath et al. Synthetic lipoteichoic acid from *Staphylococcus aureus* is a potent stimulus of cytokine release. J Exp Med. Jun. 17, 2002; 195(12):1635-40.) describe the synthesis of a complete LTA molecule with six glycerophosphate units carrying four alanine plus one N-acetyl-glucosamine substituent, which displayed the same potency to activate monocytes as native LTA. However, 100-1,000 times higher concentrations of the lipid anchor were required for cytokine induction. Of note, this synthetic molecule was not developed as a therapeutic agents but to prove the hypothesis that LTA has pro-inflammatory activity. Furthermore, the complexity of the synthetic steps involved in producing their synthetic LTA precludes the use of this material as a vaccine.

Wang et al (in Wang Y, Huebner J, Tzianabos A O, Martirosian G, Kasper D L, Pier G B. Structure of an antigenic teichoic acid shared by clinical isolates of *Enterococcus faecalis* and vancomycin-resistant *Enterococcus faecium*. Carbohydr Res. Mar. 31, 1999; 316(1-4):155-60) describe a shared antigenic teichoic acid, previously found to be a surface capsule-like poly-saccharide, from clinical isolates of *Enterococcus faecalis* and vancomycin-resistant *E. faecium*. It was composed of glucose, glycerol, and phosphate as determined by chemical and GC-MS analysis. The repeating-unit structure was elucidated by a series of 1H, 13C, and 31P NMR spectroscopy.

Deininger S et al. (in Deininger et al., Use of synthetic derivatives to determine the minimal active structure of cytokine-inducing lipoteichoic acid. Clin Vaccine Immunol. December 2007; 14(12):1629-33. Epub Oct. 10, 2007) describe that the chemical synthesis of LTA proved its immunostimulatory properties. To determine the minimal active structure of LTA, they reduced synthetic LTA in a number of steps down to the synthetic anchor and employed these molecules to stimulate interleukin-8 (IL-8) release in human whole blood. Ten times more of the synthetic structures with four to six d-alanine-substituted polyglycerophosphate units (50 nM) than of the native LTA preparation was required to induce IL-8 release. A further reduction to three backbone units with two or no d-alanine residues resulted in cytokine induction only from 500 nM. When the LTA derivatives were used at 500 nM, they induced increasing levels of IL-8 and tumor necrosis factor alpha with increasing elongation of the backbone. TLR2 dependency could be shown only with cells from TLR2-deficient mice for the two largest synthetic structures. This was confirmed by using TLR2-transfected HEK 293 cells. Taken together, these data indicate that although the synthetic anchor (which, unlike the native anchor, contains only myristic acid) cannot induce cytokine release, the addition of three backbone units, even without d-alanine substituents, confers this ability. Lengthening of the chain with d-alanine-substituted backbone units resulted in increased cytokine-inducing potency and a more sensitive response.

In the elucidation of the molecular mode of action of LTAs in effecting an immune response, pure and well-defined fragments would be valuable tools. Furthermore, an effective synthesis would also allow to produce sufficient amounts of material as needed. It is therefore an object of the present invention to provide pure and well-defined effective synthetic fragments (mimetics) of LTA, in particular in order to develop a new promising vaccine for an active or passive immunotherapy of bacteria, and in particular *enterococci*. Furthermore, improved methods for an automated synthesis shall be provided.

The present invention fulfils these needs by providing new synthetic lipoteichoic acid (LTA) mimetic having the following general formula (I)

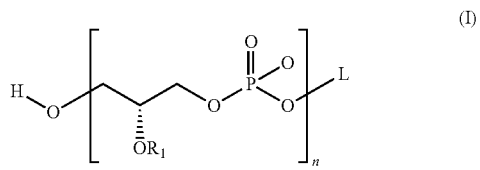

(I)

wherein $R_1$ is selected from H or a carbohydrate moiety, such as, for example, a glucosyl moiety (Glc), L is a linker moiety for connecting said mimetic to a suitable carrier protein, and n is an integer selected from 2 to 40, preferably selected from 4 to 6, or salts or solvates thereof.

This synthetic LTA cell wall mimetic provides a new and effective antigenic target for the development of more efficient strategies to effectively treat and/or prevent infection in vertebrates caused, at least in part, by *enterococci* or other gram-positive bacteria, allows for improved vaccination strategies, and allows the development and production of respective vaccines, such as glycoconjugate vaccines.

The inventors set out to develop a synthetic methodology to efficiently assemble LTA types of glycopolymers. In this respect it is of interest to note that structure and activity studies of synthetic derivatives of *Staphylococcus aureus* lipoteichoic acid (LTA) fragments led to the discovery of ligands for the human TLR-2 receptor (see, for example, Morath et al. and Deininger S et al. as cited above). The inventors directed their first attention at the TA of *Enterococcus faecalis*, which is build up from 1,3-poly(glycerolphosphate) randomly decorated at the C-2 positions with D-alanine, kojibio se (α-D-glucopyranosyl-(1→2)-α-D-glucose), or 6,6'-di-alanyl-α-kojibiose.

The above compounds include a linker group L in order to be coupled or conjugated to other chemical entities. These linker groups are known in the state of the art, and usually are immunologically inactive, i.e. do not interfere with the immunological properties of the synthetic LTA mimetic. Preferred linkers include, but are not limited to, $C_1$ to $C_{12}$ alkylamino linkers, which are optionally substituted with other groups, or peptide linkers. Other modifications include the addition of chemical moieties to the LTA mimetic (also included in "L") in order to carry a detectable label, such as chelating groups or enzymatic groups. Furthermore, peptide (e.g. His) or other "labels" or "tags" can be added in order to be able to purify and/or use the synthetic LTA mimetic, for example in diagnostic assays. Thus, preferred is a synthetic lipoteichoic acid (LTA) mimetic according to the present invention, wherein L is selected from an alkylamino group having the general formula (II)

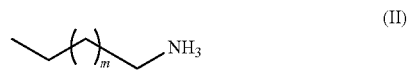

(II)

wherein m is an integer selected from 1 to 20.

The synthetic lipoteichoic acid (LTA) mimetic according to the present invention furthermore include carbohydrate moieties, such as, for example, a glucosyl (Glc) moiety. Preferably, these carbohydrate moieties units are selected from monosaccharide or disaccharide units as found in *enterococci* or *staphylococci*, such as glucose (Glu), glucosamine, N-acetyl glucosamine, galactose, rhamnose, gentiobiose, or kojibiose.

Further preferred is a synthetic lipoteichoic acid (LTA) mimetic according to the present invention, having the following general formula (III)

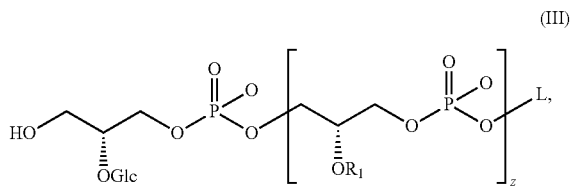

(III)

wherein z is an integer selected from 1 to 40, and preferably selected from 4 to 6.

Also further preferred is a synthetic lipoteichoic acid (LTA) mimetic according to the present invention, having the following general formula (IV)

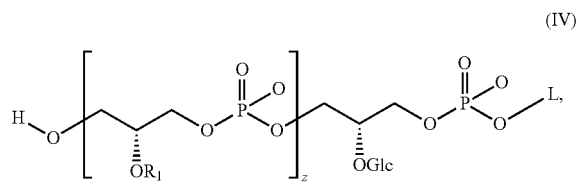

wherein z is an integer selected from 1 to 40, and preferably selected from 4 to 6.

In both these embodiments, L preferably is

Nevertheless, of course this group can also be used with the other synthetic lipoteichoic acid (LTA) mimetics of the present invention. Further preferred are compounds WH6 and WH7 as described herein (see Figures).

In general, the synthetic lipoteichoic acid (LTA) mimetic according to the present invention includes 2 to 40 repeating polyglycerol phosphate units, such as, for example, 3, 4, 5, or 6, or 10 to 20. Although it is speculated that the immunologic activity of said molecule increases with its length of polyglycerol phosphate units, the inventors could show that shorter molecules can already be quite effective in their immune response (such as, for example, hexamers, see examples). Due to the fact that these molecules are easier to synthesize, a molecule wherein n or z is 5 or 6 is most preferred.

Another aspect of the invention then relates to a pharmaceutical composition, comprising at least one of the synthetic lipoteichoic acid (LTA) mimetic according to the present invention and/or at least one antibody according to the present invention as described below, together with at least one pharmaceutically acceptable carrier, adjuvant and/or diluent.

Particularly preferred is a pharmaceutical composition according to the present invention, wherein said composition comprises a synthetic lipoteichoic acid (LTA) mimetic as described herein.

Further preferred is a pharmaceutical composition according to the present invention, wherein said composition is formulated as a vaccine, in particular against infections caused by *enterococci*, in particular antibiotic resistant *enterococci*, such as VRE strains, preferably of *E. faecalis* or *E. faecium*. Most preferred is a pharmaceutical composition according to the present invention, wherein said synthetic lipoteichoic acid (LTA) mimetic according to the present invention is present in a glycoconjugate vaccine.

The synthetic lipoteichoic acid (LTA) mimetic according to the present invention (either present as the antigen alone or in a bacterial extract or cell wall fraction) is preferably used for an *enterococcal, staphylococcal*, or pneumococcal vaccine, either for active or passive immunization.

Thus the invention further provides a pharmaceutical composition, and in particular a vaccine, for the prevention of *enterococcal* infections in a vertebrate, said pharmaceutical composition comprising at least one synthetic lipoteichoic acid (LTA) mimetic according to the present invention, optionally together with a pharmaceutically acceptable carrier, adjuvants and/or diluent. Preferred carriers include, but are not limited to, CRM (CRM197), *Tachypleus tridentatus* hemocyanin (TTH), *Limulus polyphemus* hemocyanin (LPH), tetanus toxoid (TT), diphtheria toxoid (DT), bovine serum albumin (BSA), and the ExoU protein.

Typically, the vaccine can further comprise live or dead intact cells of at least one *enterococcal* strain, preferably of *E. faecalis*, together with the synthetic lipoteichoic acid (LTA) mimetic of the invention. More typically, the vaccine comprises cell lysate from at least one *enterococcal* strain. Most preferred is a glycoconjugate vaccine comprising the synthetic lipoteichoic acid (LTA) mimetic according to the present invention. The methods for purifying the selected bacterial fractions containing *enterococcal* antigens are known to the person of skill. Another aspect relates to a pharmaceutical composition or vaccine, wherein the synthetic lipoteichoic acid (LTA) mimetic as included has been produced, at least in part, through chemical synthesis.

Typically, the vertebrate is a monogastric, herbivore or ruminant animal or human subject. Even more typically, the vertebrate is selected from the group consisting of human, non-human primate, murine, bovine, ovine, equine, porcine, caprine, leporine, avian, feline and canine. More typically, the vertebrate is selected from the group consisting of human, ovine, camelids, porcine, bovine, equine or canine.

The pharmaceutical composition can be formulated for administration via intramuscular, sub-cutaneous, topical or other parenteral route. In general, the microorganisms of the present invention are commensal in nature. Thus, oral administration is generally not an effective route of vaccination, and as a consequence, administration via an intramuscular, subcutaneous topical or other parenteral route is preferred. Preferably, the vaccine is formulated for administration via intramuscular, subcutaneous, or inhalation routes. The vaccine may also include cytokines, such as: G-CSF, GM-CSF, interleukins or tumor necrosis factor alpha, used singly or in combination.

The pharmaceutical composition may also include an adjuvant. More typically, the adjuvant is selected from the group consisting of Freunds Complete/Incomplete Adjuvant, Montenide Macrol Adjuvant, Phosphate Buffered Saline and Mannan oil emulsions, saponins (QuiLA) dextran (dextran sulphate, DEAE-Dextran), aluminum compounds (Imject Alum), N-acetylglucosamiyl-N-acetylmuramyl-L-alanyl-D-isoglutamine (Gerbu adjuvant). More typically, the adjuvant is selected from the group as described in the Vaccine 1995, vol 13, page 1203; 1993 vol 11 page 293; and 1992 vol 10 page 427, the disclosures of which are incorporated herein by reference.

Yet another important aspect of the present invention then relates to the synthetic lipoteichoic acid (LTA) mimetic according to the present invention, the antibody according to the present invention, or the pharmaceutical composition according to the present invention for use in the treatment of diseases, such as bacterial infections, in particular by a Gram-positive bacterium, such as, for example, bacterial infection, *enterococcal* infection, urinary tract infections, bacteremia, endocarditis, bacterial endocarditis, peritonitis, wound and soft tissue infections, and meningitis, or pneumonia, and foreign body infections. Said Gram-positive bacterium can be preferably selected from *enterococci, staphylococci* or *streptococci*, such as, for example, *E. faecium, E. faecalis, S. aureus*, coagulase-negative *staphylococci* or *S. pyogenes*, and in particular antibiotic-resistant strains thereof.

Another aspect of the invention then relates to a method for producing the synthetic lipoteichoic acid (LTA) mimetic of the invention, wherein said method comprises synthesizing said mimetic through chemical synthesis, comprising, for example, solution phase and/or solid phase chemistry. In the context of the experiments of the present invention, kojibiosyl-glycerol phosphoramidite in combination with a glycerolphosphoramidite, an aminohexyl-phosphoramidite and dibenzylglycerol were coupled to a fully protected glycerol TA hexamer, using chemistry that can be amended for automated synthesis. Global deprotection afforded the desired hexamer.

Preferred is a method for producing the synthetic lipoteichoic acid (LTA) mimetic according to the present invention, comprising synthesizing said molecule on a solid phase material. The methods of the present invention more preferably are in an automated solid-phase synthesis format. Such a format has been developed by the inventors and used to construct WH6 (FIG. 1) and WH7 (FIG. 2), employing commercially available automated DNA/RNA synthesis equipment in combination with tailor made glycerol phosphoramidite building blocks.

Another aspect of the invention relates to an antibody, preferably a monoclonal antibody or antigenic fragment thereof, that specifically recognizes the synthetic lipoteichoic acid (LTA) mimetic according to the present invention. The term "antibody" shall include both monoclonal or polyclonal antibodies, recombinant antibodies or fragments thereof, such as Fab and the like, as well as human or humanized antibodies.

Another aspect of the invention then relates to a method for producing the antibody according to the present invention, comprising immunizing a mammal, preferably a rabbit, with the synthetic lipoteichoic acid (LTA) mimetic according to the present invention, or a with the pharmaceutical composition according to the present invention, or preferably the vaccine according to the present invention, and, optionally isolating said antibody from said animal. Respective methods are known to the person of skill, and are disclosed in the state of the art.

Yet another aspect of the present invention then relates to a method for producing a monoclonal antibody according to the present invention that is specific for the synthetic lipoteichoic acid (LTA) mimetic according to the present invention, comprising generating hybridoma cells producing said antibody as a monoclonal antibody, or comprising a recombinant production of said antibody in a host cell. Respective methods are known to the person of skill, and are described in the state of the art.

Still another important aspect of the present invention then relates to the use of the synthetic lipoteichoic acid (LTA) mimetic according to the present invention as an antigen in the production of antibodies that are specific for said antigen.

Yet another important aspect of the present invention then relates to the use of the synthetic lipoteichoic acid (LTA) mimetic according to the present invention, the antibody according to the present invention, or the pharmaceutical composition according to the present invention for the treatment against bacterial infections or for the production of a medicament for the prophylactic or therapeutic treatment of a disease or condition caused by bacterial infections, in particular *enterococcal* infection, such as nosocomial infection, bacteraemia, endocarditis, urinary tract infections, surgical wound infections, peritonitis, wound and soft tissue infections, meningitis, pneumonia, and foreign body infections, in particular caused by antibiotic resistant *enterococci*, such as VRE strains, such as *E. faecalis*, and also *staphylococci* and *streptococci*. Preferably, said medicament is a vaccine as described herein.

According to yet another preferred embodiment of the invention, there is provided a method for inducing an immune response against at least one Gram-positive bacterial strain, such as an *enterococcal* strain, comprising the synthetic lipoteichoic acid (LTA) mimetic of the present invention in a vertebrate, said method comprising administering to said vertebrate an immunologically effective amount of the vaccine in accordance with the invention, or a pharmaceutical composition in accordance with the invention.

According to yet another preferred embodiment of the invention, there is provided a method for treating or preventing a bacterial infection in a vertebrate, comprising administering to said vertebrate a therapeutically effective amount of the synthetic lipoteichoic acid (LTA) mimetic according the present invention, the antibody according to the present invention, or the pharmaceutical composition according to the present invention.

Preferred is a method according to the present invention, wherein said bacterial infection, in particular *enterococcal* infection, is a nosocomial infection, bacteraemia, endocarditis, urinary tract infections, surgical wound infections, peritonitis, wound and soft tissue infections, meningitis, pneumonia, or foreign body infections, in particular caused by antibiotic resistant *enterococci*, such as VRE strains, such as *E. faecalis, Staphylococci* or *Streptococci*.

The present invention will now be further described in the following preferred non-limiting examples with reference to the accompanying figures. For the purposes of the present invention, all references as cited herein are incorporated in their entireties.

Figure 3:
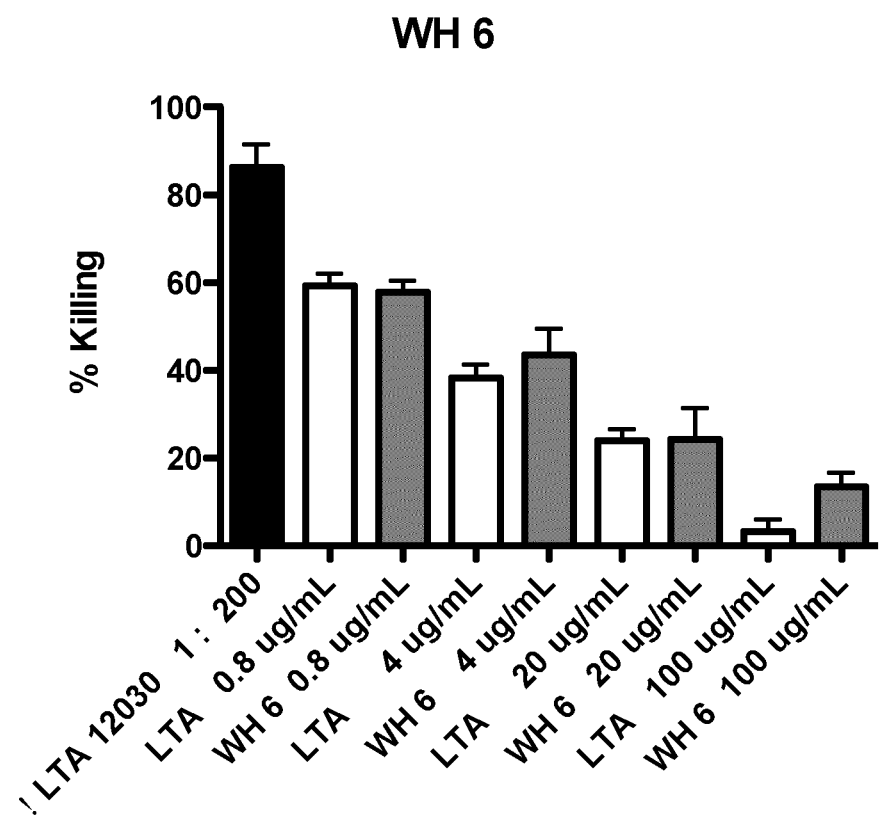

FIG. 3 shows the inhibition of opsonophagocytic killing of anti-LTA rabbit antiserum with the synthetic LTA mimetic WH 6. The black bar represents the opsonic killing of anti-LTA sera at a 1:200 dilution. Different amounts of purified LTA (white bars) and WH6 (gray bars) were added leading to a significant and dose-depended inhibition of killing.

Figure 4:
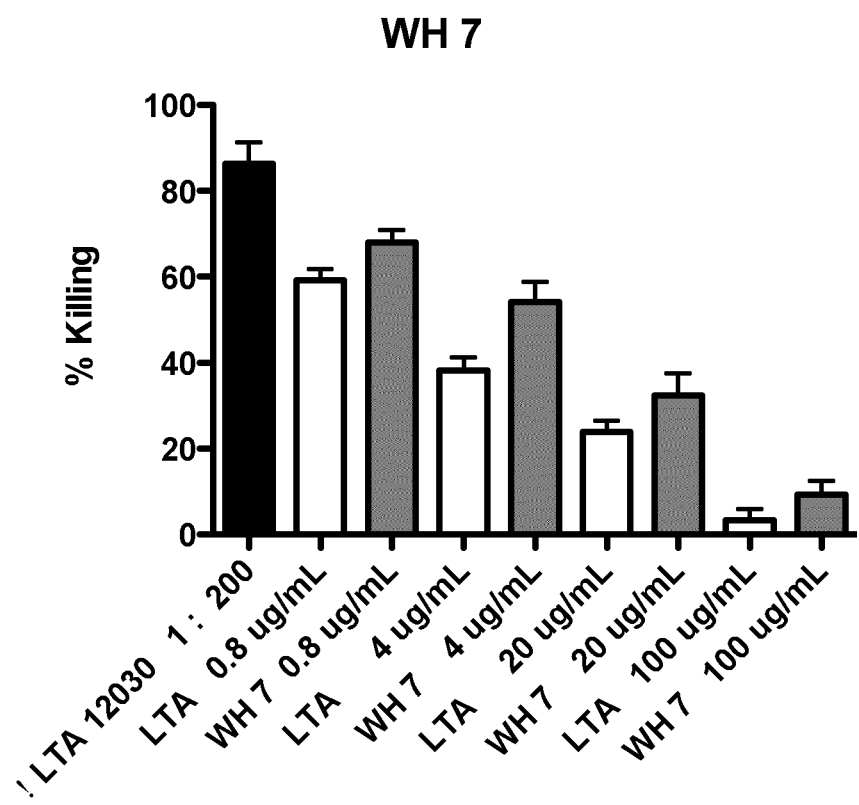

FIG. 4: Inhibition of opsonophagocytic killing of anti-LTA rabbit antiserum with the synthetic LTA mimetic WH 7. The black bar represents the opsonic killing of anti-LTA sera at a 1:200 dilution. Different amounts of purified LTA (white bars) and WH6 (gray bars) were added leading to a significant and dose-depended inhibition of killing.

EXAMPLES

Two novel structures were synthesized as follows:

Aminopropyl modified controlled pore glass support (CPG, Fluka) was loaded with 1-O-(triethylammonium succinate)-2-O-(2,3-di-O-benzyl-4,6-O-benzylidene-α-D-glucopyranosyl)-3-O-(4,4'-dimethoxytrityl)-sn-glycerol or 1-O-(triethylammonium succinate)-2-O-benzyl-3-O-(4,4'-dimethoxytrityl)-sn-glycerol (loading: 100 µmol/g CPG).

The automated syntheses were performed on a synthesizer (AKTA oligopilot plus, GE Healthcare) on a scale of 100-150 mg functionalized CPG (10-15 µmol glycerol derivative) and started with a detritylation step (3% dichloroacetic acid in toluene 15 ml, 3 min), followed by flushing with acetonitrile. Elongation was performed using 1-O—([N,N-diisopropylamino]-2-cyanoethoxy-phosphite)-2-O-benzyl-3-O-(4,4'-dimethoxytrityl)-sn-glycerol or 1-O—([N,N-diisopropylamino]-2-cyanoethoxy-phosphite)-2-O-(2,3-Di-O-benzyl-4,6-O-benzylidene-α-D-glucopyranosyl)-3-O-(4,4'-dimethoxytrityl)-sn-glycerol (0.1 M in ACN, 0.5 ml, 5 eq)

and 5-benzylthiotetrazole (BTT, 0.3M in acetonitrile, 0.75 ml, 22.5 eq) for 5 min using a cycled flow.

After flushing with acetonitrile, oxidation of the resulting phosphite was performed using $I_2$ (0.05 M in pyridine/$H_2O$ 9/1, 2 ml, 10 eq, 1 min) and a detritylation step was performed using the before mentioned cocktail.

The average coupling efficiency was measured by quantitative UV-detection (400 nm) of the dimethoxytrityl cation during each detritylation step. When the desired length was obtained, benzyl 6-([N,N-diisopropylamino]-2-cyanoethoxy-phosphite)-hexyl-1-carbamate (0.1 M in ACN, 2×0.5 ml, 2×5 eq, 2×5 min) was coupled to the CPG-TA-oligomer using BTT (0.3M in acetonitrile, 2×0.75 ml, 2×22.5 eq).

Cleavage from the resin was affected by treatment ammonia (25% in $H_2O$, 10 ml, 1 hr, the cyanoethyl protecting groups are concomitantly released at this stage). The solvents were removed in vacuo.

LC-MS analysis (column: Gemini C-18, dimensions 4.6/5 mm, eluent: (10 mM $NH_4OAc$ in $H_2O$)/acetonitrile, 9/1→1/1, detection: UV (215 and 254 nm) was used to check the integrity of the semiprotected oligomer.

The TA fragments were purified using anion-exchange chromatography (AKTA Explorer, GE Healthcare; column: Q-sepharose HR16/10, GE Healthcare; eluent: buffer A (50 mM NaOAc, 50 mM $NaClO_4$), buffer B (50 mM NaOAc, 500 mM $NaClO_4$), gradient 1/0→0/1)) followed by desalination using size-exclusion chromatography (Sephadex G25, GE Healthcare, dimensions: 26/60 mm, eluent: 0.15 M $NH_4HCO_3$).

The purified oligomer was lyophilized two times before it was eluted through a small column containing Dowex Na+ cation-exchange resin (type: 50WX4-200, stored on 0.5 M NaOH in $H_2O$). Deprotection was performed by treating the oligomers (1-5 μmol) for 3 days with Palladium black (20-40 mg)/$H_2$ in $H_2O$ (3-6 ml) together with AcOH (3-6 drops). Subsequently, the mixture was filtered and the solvents removed under reduced pressure before the residue was purified by size-exclusion chromatography (Sephadex HW40, Toyopearl, dimensions: 16/60 mm, eluent: 0.15 M $Et_3NHOAc$ or 0.15 M $NH_4OAc$). After repeated lyophilisation (twice), the product was eluted through a small column containing Dowex $Na^+$ cation-exchange resin (type: 50WX4-200, stored on 0.5 M NaOH in $H_2O$).

Figure 1:
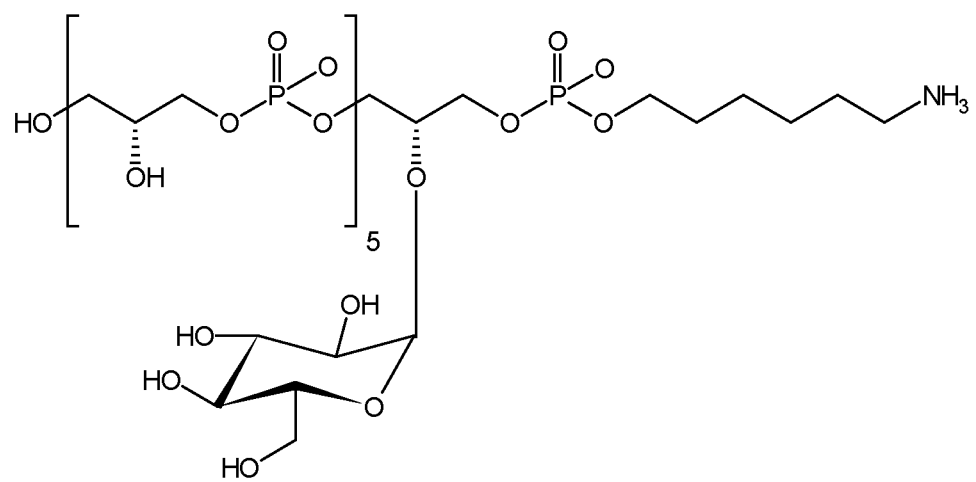
FIG. 1 shows the structure of the synthetic LTA mimetic WH6 according to the invention.

Synthesis of Compound WH 6 (See FIG. 1):

Synthesis on 15 μmol scale (150 mg glycerol resin). Average coupling efficiency: 98.2% (5 couplings). LC-MS indicated clean product formation gradient: 10 mM $NH_4OAc$ in $H_2O$/acetonitrile 1/0=1/9, r.t. 7.60 min, $[C_{94}H_{119}NO_{38}P_6+H]^{2+}$ requires 1029.3 found 1029.2.

The purification gave the semiprotected hexamer as white amorphous solid (10.5 mg, 32%). $^{31}$P-NMR (162 MHz, $D_2O$): δ=1.0 (1P), 1.1 (3P), 1.1 (1P), 1.2 (1P); $^1$H-NMIR (600 MHz, $D_2O$): δ=0.85-1.17 (m, 6H, 3×$CH_2$ hexylspacer), 1.37 (m, 2H, $CH_2$ hexylspacer), 2.84 (m, 2H, $CH_2$—N hexylspacer), 3.34-4.11 (m, 38H, $CH_2$—O hexylspacer, 12×$CH_2$ glycerol, 6×CH glycerol, H-2, H-3, H-4, H-5, 2×H-6), 4.29-4.71 (m, 16H, 7×$CH_2$Bn, $CH_2$ benzylcarbamate), 6.86-7.43 (m, 45H, Harom); HRMS: $[C_{94}H_{119}NO_{38}P_6+NH_4+H]_2^+$ requires 1037.3123. found 1037.3120.

Deprotection: The partially protected hexamer (10.5 mg, 4.87 μmol) was deprotected using the standard procedure yielding hexamer monoglucosylglycerol TA WH7 (4.37 mg, 75%) as an amorphous off-white solid. $^{31}$P-NMR (162 MHz, $D_2O$): δ=0.9 (1P), 1.2 (3P), 1.3 (1P), 1.3 (1P); $^1$H-NMR (600 MHz, $D_2O$): δ=1.36-1.40 (m, 4H, 2×$CH_2$ hexylspacer), 1.58-1.65 (m, 4H, 2×$CH_2$ hexylspacer), 2.94 (at, 2H, J=7.5 Hz, $CH_2$—N hexylspacer), 3.34 (at, 1H, J=9.6 Hz, H-4), 3.46 (dd, 1H, J=3.7 Hz, 9.9 Hz, H-2), 3.55 (dd, $^1$H, J=6.1 Hz, 11.8 Hz, CHH glycerol), 3.62 (dd, 1H, J=4.2 Hz, 11.8 Hz, CHH glycerol), 3.69-3.72 (m, 3H, H-3, H-5, H-6), 3.79-4.00 (m, 30H, $CH_2$—O hexylspacer, 11×CH2 glycerol, 5×CH glycerol, H-6), 4.05 (m, 1H, CH glycerol), 5.11 (d, 1H, J=3.7 Hz, H-1); $^{13}$C NMR (150 MHz, D2O): δ=25.4, 26.1, 27.6, 30.4 (4×$CH_2$ hexylspacer), 40.4 ($CH_2$—N hexylspacer), 61.5 (C-6), 63.0 ($CH_2$ glycerol), 65.2 ($CH_2$ glycerol), 66.1 ($CH_2$ glycerol) 67.0-67.4 ($CH_2$—O hexylspacer, 9×CH2 glycerol), 70.4-70.6 (4×CH glycerol, C-4), 71.7 (CH glycerol), 72.5 (C-2), 72.8 (C-5), 73.9 (C-3), 76.3 (CH glycerol), 98.7 (C-1); HRMS: $C_{30}H_{67}NO_{36}P_6+H+$ requires 1204.1941. found 1204.1957.

Figure 2:
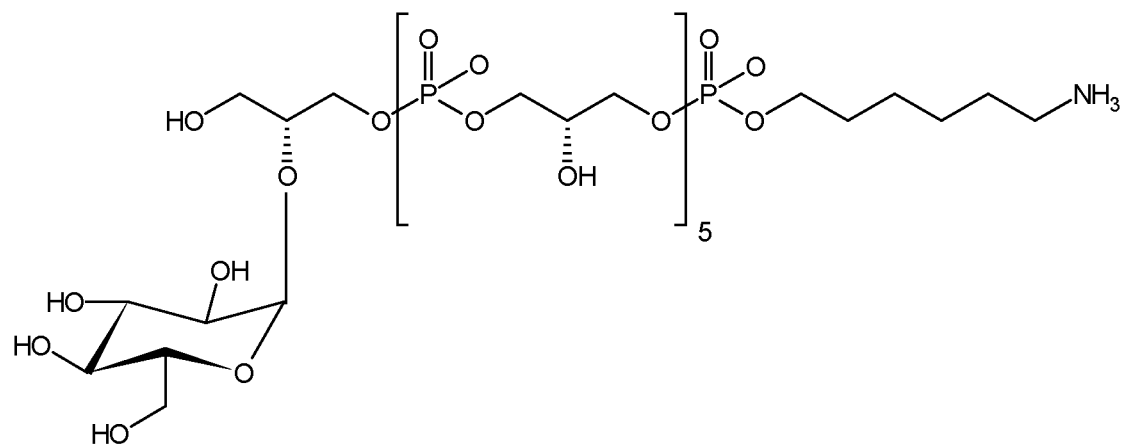
FIG. 2 shows the structure of the synthetic LTA mimetic WH7 according to the invention.

WH7 (see FIG. 2): Synthesis on 15 μmol scale (150 mg glucosyl-glycerol resin). Average coupling efficiency: 96.9% (5 couplings). LC-MS indicated clean product formation gradient: 10 mM NH4OAc in $H_2O$/acetonitrile 9/1→1/9, r.t. 6.07 min, $C_{94}H_{119}NO_{38}P_6+H+$ requires 2057.6 found 2058.0. Purification method B gave the semiprotected hexamer as white amorphous solid (11.6 mg, 36%). $^{31}$P-NMR (162 MHz, $D_2O$): δ=1.0-1.1 (4P), 1.2 (2P); $^1$H-NMR (600 MHz, $D_2O$): δ=0.90-1.15 (m, 6H, 3×$CH_2$ hexylspacer), 1.33 (m, 2H, $CH_2$ hexylspacer), 2.80 (m, 2H, $CH_2$—N hexylspacer), 3.22-4.18 (m, 38H, CH2-O hexyl-spacer, 12×$CH_2$ glycerol, 6×CH glycerol, H-2, H-3, H-4, H-5, 2×H-6), 4.30-4.69 (m, 16H, 7×CH2 Bn, $CH_2$ benzylcarbamate), 6.86-7.26 (m, 45H, H$_{arom}$); HRMS: $[C_{94}H_{119}NO_{38}P_6+H]^{2+}$ requires 1028.7991. found 1028.7996; Deprotection: The partially protected hexamer (2.23 mg, 0.987 μmol) was deprotected using the standard procedure yielding hexamer monoglucosylglycerol TA WH6 (1.12 mg, 90%) as an amorphous off-white solid. 31P-NMR (162 MHz, $D_2O$): δ=1.2 (1P), 1.2 (3P), 1.3 (1P), 1.3 (1P); 1H-NMR (600 MHz, $D_2O$): δ=1.36-1.40 (m, 4H, 2×CH2 hexylspacer), 1.59-1.65 (m, 4H, 2×$CH_2$ hexylspacer), 2.94 (at, 2H, J=7.5 Hz, CH2-N hexylspacer), 3.36 (at, 1H, J=9.7 Hz, H-4), 3.48 (dd, 1H, J=3.8 Hz, 9.9 Hz, H-2), 3.68-3.73 (m, 4H, H-3, 2×H-6, CHH glycerol), 3.77-4.02 (m, 32H, $CH_2$—O hexylspacer, 11×$CH_2$ glycerol, CHH glycerol, 6×CH glycerol, H-5), 5.12 (d, 1H, J=3.7 Hz, H-1); $^{13}$C NMR (150 MHz, D2O): δ=25.4, 26.0, 27.6, 30.3 (4×$CH_2$ hexylspacer), 40.4 ($CH_2$—N hexylspacer), 61.5 ($CH_2$ glycerol), 62.2 (C-6), 65.2 ($CH_2$ glycerol), 66.9-67.2 ($CH_2$—O hexylspacer, 11×$CH_2$ glycerol), 70.4-70.6 (5×CH glycerol, C-4), 72.4 (C-2), 72.9 (C-5), 73.8 (C-3), 77.8 (CH glycerol), 98.8 (C-1); HRMS: $C_{30}H_{67}NO_{36}P_6+H^-$ requires 1204.1941. found 1204.1956.

The opsonophagocytic assay is the best surrogate for the protective immune response against bacterial pathogens. Rabbit sera raised against LTA purified from *E. faecalis* 12030 are able to effectively kill the homologous strain as well as a subset of about 25% of *E. faecalis* and *E. faecium*. Absorption of this serum with purified LTA inhibits killing (Theilacker, Kaczynski et al. 2006). Using this approach we were able to inhibit killing of the anti-LTA serum with two synthetic LTA backbone structures substituted with glucose molecules in different position (see FIGS. 1 and 2).

Inhibition with WH6 (see FIG. 1) and WH7 (see FIG. 2) resulted in complete inhibition comparable to wild-type full-length LTA (see FIGS. 3 and 4; white bars).

Six different LTA mimetics that were tested in a similar fashion did not show significant or dose-depended inhibition of killing.

The inventors therefore conclude that the LTA mimetics presented here are promising vaccine targets against *enterococci* and other gram-positive pathogens by conjugation of these molecules to appropriate protein carriers (such as tetanus toxoid or diphteria toxoid).

REFERENCES

J. Huebner, Y. Wang, W. A. Krueger, L. C. Madoff, G. Martirosian, S. Boisot, D. A. Goldmann, D. L. Kasper, A. O. Tzianabos and G. B. Pier (1999). "Isolation and chemical characterization of a capsular polysaccharide antigen shared by clinical isolates of *Enterococcus faecalis* and vancomycin-resistant *Enterococcus faecium.*" *Infect Immun* 67(3): 1213-1219.

J. Huebner, A. Quaas, W. A. Krueger, D. A. Goldmann and G. B. Pier (2000). "Prophylactic and therapeutic efficacy of antibodies to a capsular polysaccharide shared among vancomycin-sensitive and -resistant *enterococci.*" *Infect Immun* 68(8): 4631-4636.

C. Theilacker, Z. Kaczynski, A. Kropec, F. Fabretti, T. Sange, O. Holst and J. Huebner (2006). "Opsonic antibodies to *Enterococcus faecalis* strain 12030 are directed against lipoteichoic acid." *Infect Immun* 74(10): 5703-5712.

I. G. Sava, E. Heikens and J. Huebner (2010). "Pathogenesis and immunity in *enterococcal* infections." *Clin Microbiol Infect* 16(6): 533-540.

W. F. Hogendorf, L. J. Bos, H. S. Overkleeft, J. D. Codee and G. A. Marel (2010). "Synthesis of an alpha-kojibiosyl substituted glycerol teichoic acid hexamer." *Bioorg Med Chem* 18(11): 3668-3678.

The invention claimed is:

1. A synthetic lipoteichoic acid (LTA) mimetic having the following general formula (I):

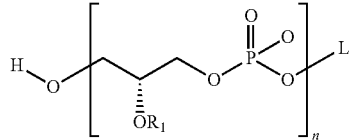
(I)

wherein $R_1$ is selected from H or a carbohydrate moiety,

L is a linker moiety for connecting said mimetic to a carrier protein, wherein L is an alkylamino group having the general formula (II)

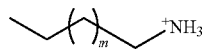
(II)

wherein m is an integer selected from 1 to 20, and n is an integer selected from 2 to 40, or a salt or solvate thereof; and wherein the LTA mimetic is optionally linked to a carrier protein through the linker moiety L.

2. The synthetic lipoteichoic acid (LTA) mimetic according to claim 1, wherein said carbohydrate moiety is a glucosyl moiety (Glc) selected from a monosaccharide or disaccharide unit.

3. A synthetic lipoteichoic acid (LTA) mimetic, having the following general formula (III)

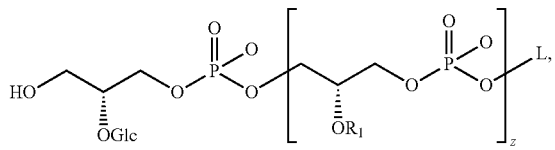
(III)

wherein z is an integer selected from 1 to 40, $R_1$ is selected from H or a carbohydrate moiety, L is a linker moiety for connecting said mimetic to a carrier protein, wherein L is an alkylamino group having the general formula (II)

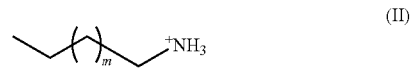
(II)

wherein m is an integer selected from 1 to 20, or a salt or solvate thereof; and wherein the synthetic lipoteichoic acid (LTA) mimetic is optionally linked to a carrier protein through the linker moiety L.

4. The synthetic lipoteichoic acid (LTA) mimetic according to claim 1, having the following general formula (IV)

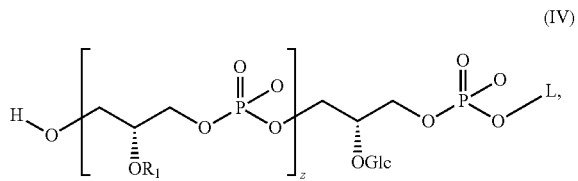
(IV)

wherein z is an integer selected from 1 to 40.

5. The synthetic lipoteichoic acid (LTA) mimetic according to claim 1, wherein n is 5 or 6.

6. A pharmaceutical composition, comprising a synthetic lipoteichoic acid (LTA) mimetic having the following general formula (I):

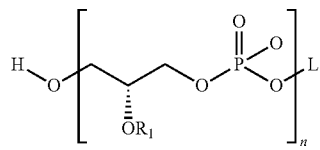
(I)

wherein $R_1$ is selected from H or a carbohydrate moiety,

L is a linker moiety for connecting said mimetic to a carrier protein, wherein L is an alkylamino group having the general formula (II)

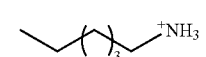
(II)

wherein m is an integer selected from 1 to 20, and n is an integer selected from 2 to 40, or a salt or solvate thereof; wherein the synthetic lipoteichoic acid (LTA) mimetic is optionally linked to a carrier protein through the linker moiety L, and a pharmaceutically acceptable carrier, adjuvant and/or diluent.

7. The pharmaceutical composition according to claim 6, wherein said composition is formulated as a vaccine.

8. The pharmaceutical composition according to claim 6, further comprising at least one cytokine.

9. The pharmaceutical composition according to claim 7, wherein said vaccine is formulated for administration via a route selected from intramuscular, subcutaneous, and inhalation.

10. A method for producing an LTA mimetic according to claim 1, wherein the synthesis is performed entirely on a solid phase material, followed by cleavage from the solid phase material, and purification.

11. A method for producing an antibody that specifically binds to an LTA molecule according to claim 1, comprising immunizing a suitable animal with an LTA molecule according to claim 1, and isolating said antibody from said animal.

12. A method for treating a disease or condition caused by a bacterium, wherein said method comprises administering, to a subject in need of such treatment, an LTA molecule of claim 1.

13. The method, according to claim 12, wherein the bacterium is Gram-positive.

14. The method, according to claim 13, wherein the bacterium is selected from *enterococci, staphylococci* and *streptococci*.

15. The method, according to claim 12, wherein the bacterium is selected from *E. faecium, E. faecalis, S. aureus*, coagulase-negative *staphylococci, S. pyogenes, S. pneumoniae*, and *C. difficile*.

16. The method, according to claim 12, wherein the disease or condition is selected from bacterial infections, *enterococcal* infections, urinary tract infections, bacteremia, bacterial endocarditis, peritonitis, wound and soft tissue infections, meningitis, and pneumonia.

17. The method, according to claim 12, wherein the bacterium is an antibiotic-resistant strain.

18. The synthetic lipoteichoic acid (LTA) mimetic according to claim 1, wherein the mimetic is connected via said linker to a carrier protein.

* * * * *